United States Patent [19]

Fest et al.

[11] Patent Number: 4,846,879
[45] Date of Patent: Jul. 11, 1989

[54] PHENYLSULPHONYLISOUREA HERBICIDES

[75] Inventors: Christa Fest; Hans-Jochem Riebel, both of Wuppertal; Hans-Joachim Santel, Leverkusen; Robert R. Schmidt, Bergisch Gladbach; Robert H. Strang, Duesseldorf, all of Fed. Rep. of Germany

[73] Assignee: Bayer Aktiengesellschaft, Leverkusen, Fed. Rep. of Germany

[21] Appl. No.: 105,860

[22] Filed: Oct. 7, 1987

[30] Foreign Application Priority Data

Oct. 14, 1986 [DE] Fed. Rep. of Germany ....... 3634929

[51] Int. Cl.$^4$ .................. A01N 43/66; C07D 251/42; C07D 251/48; C07D 251/70
[52] U.S. Cl. ........................................ 71/93; 544/211; 544/212; 544/206; 544/207; 544/208; 544/209; 544/197; 544/198; 534/632; 534/751; 534/738
[58] Field of Search ............... 71/93; 544/211, 206, 544/208, 197, 212, 207, 209, 198; 534/632, 751, 738

[56] References Cited

U.S. PATENT DOCUMENTS 4,310,346 1/1982 Levitt et al. .................... 544/208
4,750,930 6/1988 Shapiro ........................... 544/208

Primary Examiner—John M. Ford
Attorney, Agent, or Firm—Sprung Horn Kramer & Woods

[57] ABSTRACT

Herbicidally active compounds of the formula

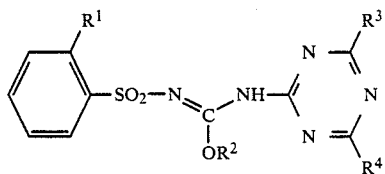

in which $R^1$ represents halogen, cyano or $C_1$–$C_6$-alkyl (which is optionally substituted by fluorine, chlorine, bromine, cyano, $C_1$–$C_4$-alkoxy, $C_3$–$C_6$-cycloalkyl or phenyl), or represents $C_1$–$C_4$-alkoxy (which is optionally substituted by chlorine, bromine, cyano or $C_1$–$C_4$-alkoxy), $R^2$ represents optionally substituted aryl, $R^3$ represents hydrogen, halogen, hydroxyl, $C_1$–$C_6$-alkylamino or di-($C_1$–$C_6$-alkyl)-amino, or represents optionally substituted $C_1$–$C_6$-alkyl, $C_1$–$C_6$-alkoxy or $C_1$–$C_6$-alkylthio, and $R^4$ represents hydrogen, halogen or hydroxyl, or represents optionally substituted $C_1$–$C_6$-alkyl, $C_1$–$C_6$-alkoxy or $C_1$–$C_6$-alkylthio, or represents $C_1$–$C_6$-alkylamino or di-($C_1$–$C_6$-alkyl)-amino, excluding the compound N'-(2-chloro-benzenesulphonyl)-N''-(4,6-dimethyl-1,3,5-triazin-2-yl)-0-phenyl-isourea.

7 Claims, No Drawings

PHENYLSULPHONYLISOUREA HERBICIDES

The invention relates to new phenylsulphonylisoureas, a process for their preparation and their use as herbicides.

It is known that certain isoureas, such as, for example, N'-(2-chloro-benzenesulphonyl)-N''-(4,6-dimethyl-1,3,5-triazin-2-yl)-O-phenyl-isourea, have herbicidal properties. The action of these compounds, however, is not always completely satisfactory (compare, for example, European Pat. No. A-173,957).

New phenylsulphonylisoureas of the general formula (I)

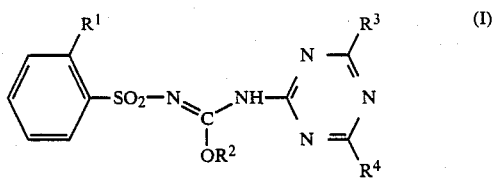

in which $R^1$ represents halogen [such as, in particular, fluorine, chlorine, bromine and/or iodine], cyano or $C_1$-$C_5$-alkyl [which is optionally substituted by fluorine, chlorine, bromine, cyano, $C_1$-$C_4$-alkoxy, $C_3$-$C_6$-cycloalkyl or phenyl], or represents $C_1$-$C_4$-alkoxy [which is optionally substituted by chlorine, bromine, cyano or $C_1$-$C_4$-alkoxy], $R^2$ represents optionally substituted aryl, $R^3$ represents hydrogen, halogen, hydroxyl, $C_1$-$C_6$-alkylamino or di-($C_1$-$C_6$-alkyl)-amino, or represents optionally substituted $C_1$-$C_6$-alkyl, $C_1$-$C_6$-alkoxy or $C_1$-$C_6$-alkylthio and $R^4$ represents hydrogen, halogen or hydroxyl, or represents optionally substituted $C_1$-$C_6$-alkyl, $C_1$-$C_6$-alkoxy or $C_1$-$C_6$-alkylthio, or represents $C_1$-$C_6$-alkylamino or di-($C_1$-$C_6$-alkyl)-amino, have now been found, the following compound being excluded however: N'-(2-chloro-benzenesulphonyl)-N''-(4,6-dimethyl-1,3,5-triazin-2-yl)-O-phenyl-isourea.

The new phenylsulphonylisoureas of the general formula (I) are obtained by a process in which iminocarbonic acid esters of the formula (II)

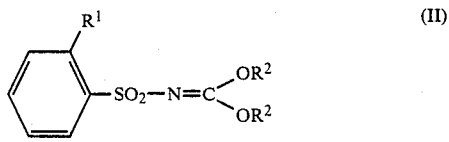

in which $R^1$ and $R^2$ have the abovementioned meanings, are reacted with 2-amino-triazines of the formula (III)

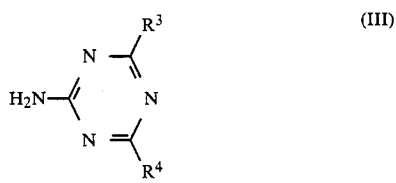

in which $R^3$ and $R^4$ have the abovementioned meanings in the presence of acid acceptors and if appropriate in the presence of diluents.

The new phenylsulphonylisoureas of the formula (I) are distinguished by a potent herbicidal activity. Surprisingly, the new compounds of the formula (I) exhibit a considerably better herbicidal action than the already known isoureas of the same type of action.

The invention preferably relates to compounds of the formula (I) in which $R^1$ represents fluorine, chlorine, bromine, cyano or $C_1$-$C_4$-alkyl [which is optionally substituted by fluorine, chlorine, bromine, cyano, $C_1$-$C_2$-alkoxy or phenyl] or represents $C_1$-$C_2$-alkoxy [which is optionally substituted by chlorine, bromine, cyano or $C_1$-$C_2$-alkoxy], $R^2$ represents a phenyl radical, which is optionally substituted by one or more radicals from the series comprising halogen [such as, in particular, fluorine, chlorine, bromine and iodine], cyano, nitro, hydroxyl, carboxyl, $C_1$-$C_6$-alkyl [which is optionally substituted by fluorine, chlorine, bromine, nitro, cyano, hydroxyl, carboxyl, $C_1$-$C_4$-alkoxy-carbonyl, $C_1$-$C_4$-alkoxy, $C_1$-$C_4$-alkylthio or phenyl], $C_3$-$C_6$-cycloalkyl, $C_1$-$C_4$-alkoxy [which is optionally substituted by fluorine, chlorine, bromine, cyano, carboxyl, $C_1$-$C_4$-alkoxy, $C_1$-$C_4$-alkylthio or $C_1$-$C_4$-alkoxy-carbonyl], $C_1$-$C_4$-alkylthio [which is optionally substituted by fluorine, chlorine, bromine, cyano, carboxyl, $C_1$-$C_4$-alkoxy-carbonyl], amino, $C_1$-$C_4$-alkyl-amino and di-($C_1$-$C_4$-alkyl)-amino [which are optionally substituted by fluorine, chlorine, bromine, cyano, carboxyl, $C_1$-$C_4$-alkoxy or $C_1$-$C_4$-alkoxy-carbonyl], $C_1$-$C_4$-alkyl-carbonyl-amino, $C_1$-$C_4$-alkoxy-carbonylamino, (di)-$C_1$-$C_4$-alkylaminocarbonylamino, formyl, $C_1$-$C_4$-alkyl-carbonyl, benzoyl, $C_1$-$C_4$-alkoxy-carbonyl, phenoxy-carbonyl, benzyloxycarbonyl, phenyl [which is optionally substituted by fluorine, chlorine, bromine, cyano, nitro, hydroxyl or methyl], phenoxy, phenylthio, phenylsulphonyl, phenylamino and phenylazo [which are optionally substituted by fluorine, chlorine, bromine, cyano, nitro, methyl and/or trifluoromethyl], pyridoxy and pyrimidoxy [which are optionally substituted by fluorine, chlorine, bromine, cyano, nitro, methyl and/or trifluoromethyl], $C_1$-$C_4$-alkyl-carbonyloxy, $C_1$-$C_4$-alkoxy-carbonyloxy, $C_1$-$C_4$-alkyl-amino-carbonyloxy and di-($C_1$-$C_4$-alkyl)-amino-carbonyloxy, or which is optionally fused by an alkylene chain [which is optionally branched and/or interrupted by one or more oxygen atoms] or a benzo radical [which is optionally substituted by fluorine, chlorine, bromine, cyano, nitro, methyl and/or trifluoromethyl];

and wherein, furthermore, $R^3$ represents hydrogen, fluorine, chlorine, bromine, hydroxyl, $C_1$-$C_4$-alkylamino, di-($C_1$-$C_4$-alkyl)-amino, $C_1$-$C_4$-alkyl [which is optionally substituted by fluorine and/or chlorine], $C_1$-$C_4$-alkoxy [which is optionally substituted by fluorine and/or chlorine] or $C_1$-$C_4$-alkylthio [which is optionally substituted by fluorine and/or chlorine] and $R^4$ represents hydrogen, fluorine, chlorine, bromine, hydroxyl, $C_1$-$C_4$-alkyl [which is optionally substituted by fluorine and/or chlorine], $C_1$-$C_4$-alkoxy [which is optionally substituted by fluorine and/or chlorine], $C_1$-$C_4$-alkylthio [which is optionally substituted by fluorine and/or chlorine], $C_1$-$C_4$-alkylamino or di-($C_1$-$C_4$-alkyl)-amino, the following compound being excluded, however: N'-(2-chloro-benzenesulphonyl)-N''-(4,6-dimethyl-1,3,5-triazin-2-yl)-O-phenyl-isourea.

Particularly preferred compounds of the formula (I) are those in which $R^1$ represents fluorine, chlorine, bromine, cyano, methyl, ethyl, trifluoromethyl, methoxy, 2-chloroethoxy or benzyl, $R^2$ represents a phenyl radical, which is optionally substituted by one or two radicals from the series comprising fluorine, chlorine, bromine, iodine, cyano, nitro, hydroxyl, carboxyl, $C_1$-$C_3$-alkoxy-carbonyl, $C_1$-$C_4$-alkyl, trifluoromethyl, hydroxymethyl, methoxycarbonylmethyl, phenyl-$C_1$-$C_3$-alkyl, cyclohexyl, $C_1$-$C_3$-alkoxy, trifluoromethoxy, $C_1$-$C_3$-alkylthio, trifluoromethylthio, dimethylamino, amino, acetylamino, methylaminocarbonyl, formyl, acetyl, benzoyl, phenyl, hydroxyphenyl, phenoxy [which is optionally substituted by chlorine and/or trifluoromethyl], phenylamino, phenylazo and pyridoxy [which is optionally substtiuted by chlorine and/or trifluoromethyl], or which is optionally benzofused;

and wherein, furthermore, $R^3$ represents fluorine, chlorine, methyl, ethyl, methoxy, ethoxy, methylthio, ethylthio, methylamino, ethylamino, dimethylamino or diethylamino, and $R^4$ represents fluorine, chlorine, methyl, ethyl, methoxy, ethoxy, methylthio, ethylthio, methylamino, ethylamino, dimethylamino or diethylamino, the following compound being excluded, however: N'-(2-chloro-benzenesulphonyl)-N''-(4,6-dimethyl-1,3,5-triazin-2-yl)-O-phenyl-isourea.

If, for example, O,O-diphenyl N-(2-chloro-benzenesulphonyl)-iminocarbonate and 2-amino-4-methoxy-6-methyl-1,3,5-triazine are used as starting substances for the process according to the invention, the course of the reaction can be represented by the following equation:

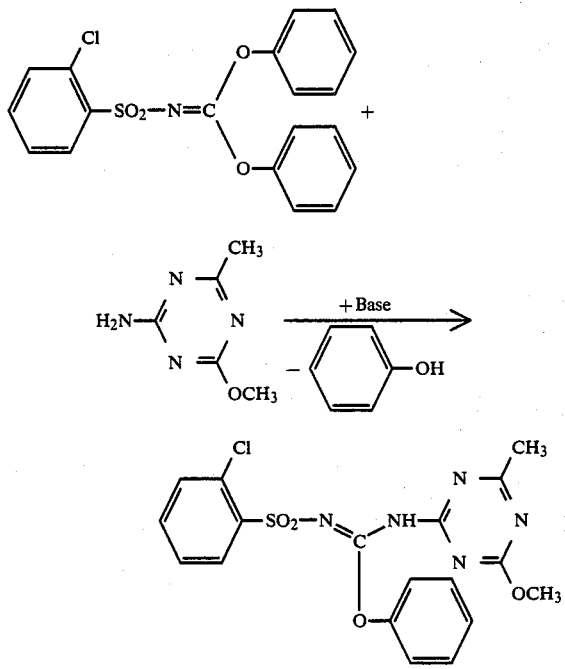

Formula (II) provides a general definition of the iminocarbonic acid esters to be used as starting substances in the process according to the invention. In this formula (II), $R^1$ and $R^2$ preferably represent those radicals which have already been mentioned as preferred for these substituents in connection with the description of the substances of the formula (I) according to the invention.

The compounds of the formula (II) are the subject of commonly assigned patent application Ser. No., filed simultaneously herewith and corresponding to German Application P No. 36 34 926.7.

The compounds of the formula (II) are obtained by a process in which iminocarbonic acid dichlorides of the formula (IV)

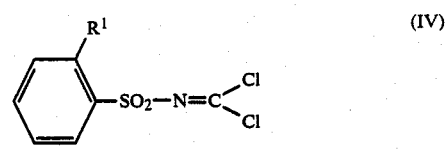

in which $R^1$ has the abovementioned meanings, are reacted with compounds of the formula (V)

$$R^2\text{—OM} \qquad (V)$$

in which $R^2$ has the abovementioned meanings and

M represents hydrogen or an alkali metal atom, if appropriate in the presence of acid acceptors, such as, for example, sodium hydroxide or potassium hydroxide, and if appropriate in the presence of inert diluents, such as, for example, acetone, methyl ethyl ketone or acetonitrile, at temperatures between 10° C. and 100° C.

The iminocarbonic acid dichlorides of the formula (IV) are known in some cases and/or can be prepared by known processes (compare, for example, Chem. Ber. 99, 2900 (1966), CA 90: 137826b; Angew. Chem. 77, 430 (1965)). New iminocarbonic acid dichlorides which are likewise the subject of commonly assigned patent application Ser. No., filed simultaneously herewith and corresponding to German Application No. P 36 34 926.7 are those of the formula (IVa)

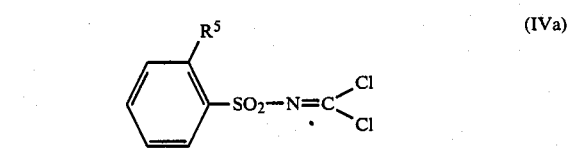

in which $R^5$ represents halogen [such as, in particular, fluorine, chlorine, bromine and/or iodine], cyano, $C_2$-$C_6$-alkyl or $C_1$-$C_6$-alkyl [which is substitted by fluorine, chlorine, bromine, cyano, $C_1$-$C_4$-alkoxy, $C_3$-$C_6$-cycloalkyl or phenyl], or represents $C_1$-$C_4$-alkoxy [which is optionally substituted by chlorine, bromine, cyano or $C_1$-$C_4$-alkoxy].

The new compounds of the formula (IVa) are obtained by a process in which dimethyl iminodithiocarbonates of the formula (VI)

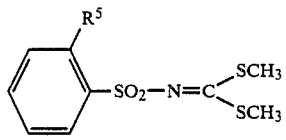  (VI)

in which

R⁵ has the meanings given above in the case of formula (IVa), are reacted with chlorinating agents, such as, for example, sulphuryl chloride or chlorine, in the presence of inert diluents, such as, for example, carbon tetrachloride, at temperatures between 0° C. and 25° C.

The dimethyl iminodithiocarbonates of the formula (VI) are known and/or can be prepared by known methods (compare, for example, European Pat. No. A-121,082, European Pat. No. A-151,554 and European Pat. No. A-173,957).

The compounds of the formula (V) which are furthermore to be employed as starting substances for the preparation of the compounds of the formula (II) are generally known compounds of organic chemistry.

Examples which may be mentioned of the iminocarbonic acid esters of the formula (II) are:

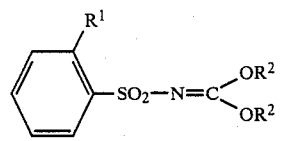  (II)

TABLE 1

| $R^1$ | $R^2$ |
|---|---|
| 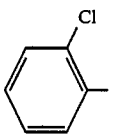 Cl | 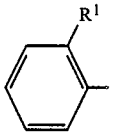 |
| 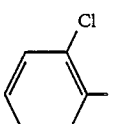 Cl | 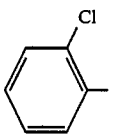 Cl |
| 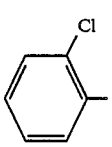 Cl | 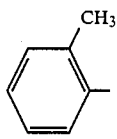 Cl |
| 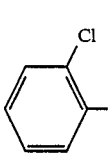 Cl | 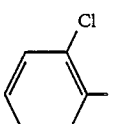 Cl |
| 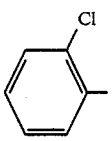 Cl | 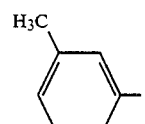 H₃C- |

TABLE 1-continued

| $R^1$ | $R^2$ |
|---|---|
| 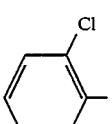 Cl | 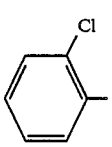 CH₃ |
| 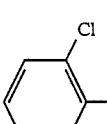 Cl | 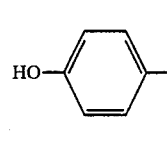 H₃C- |
| 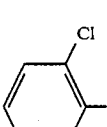 Cl | 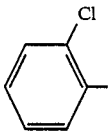 HO- |
| 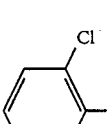 Cl | 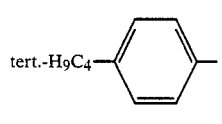 tert.-H₉C₄- |
| 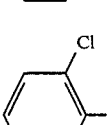 Cl | 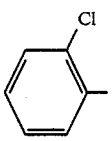 H₅C₂- |
|  Cl | 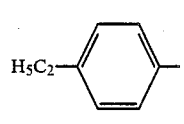 C₂H₅ |
| 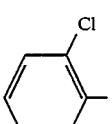 Cl | 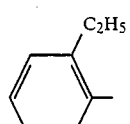 H₅C₂- |
| 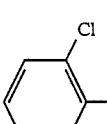 Cl | 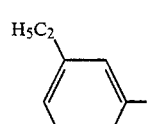 Br |
| 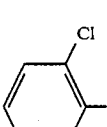 Cl | 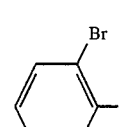 Br |
| 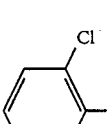 Cl | 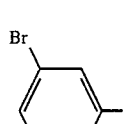 Br- |
| 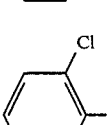 Cl | 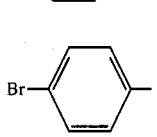 |

TABLE 1-continued
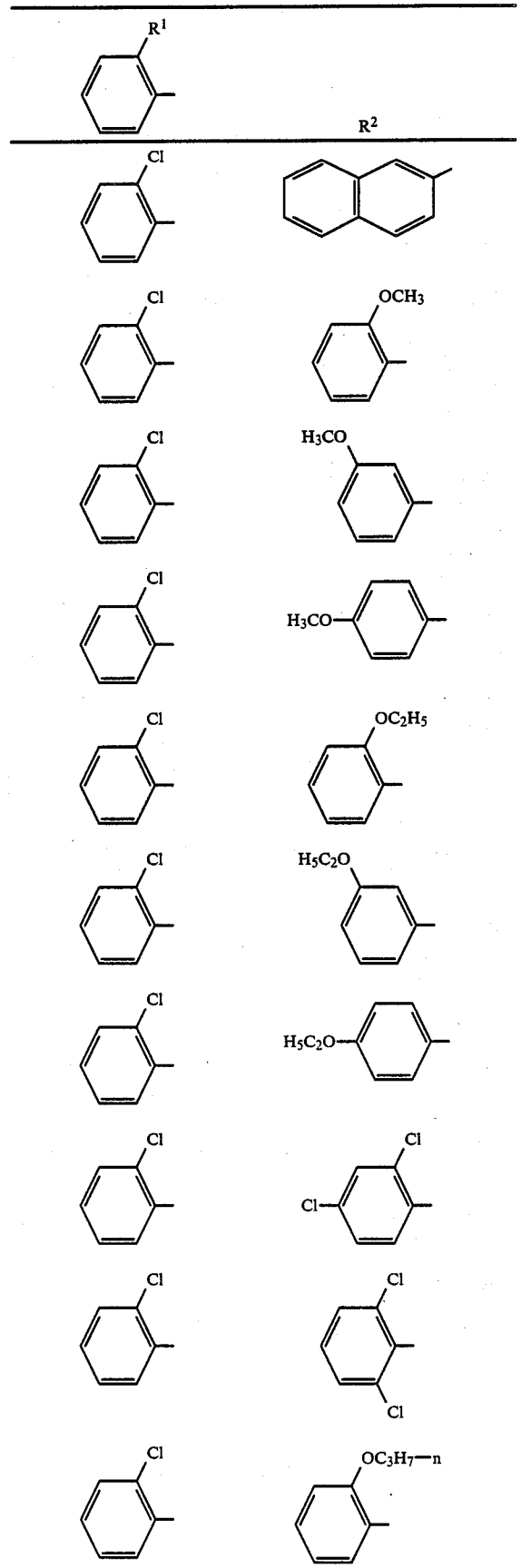
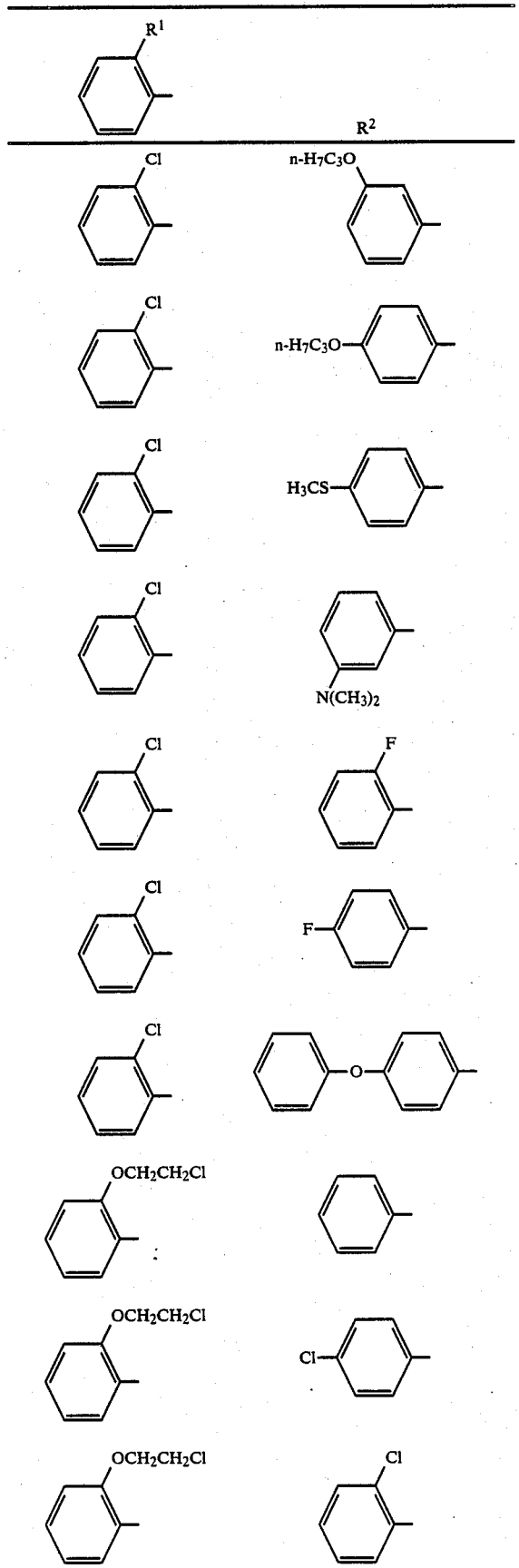

TABLE 1-continued
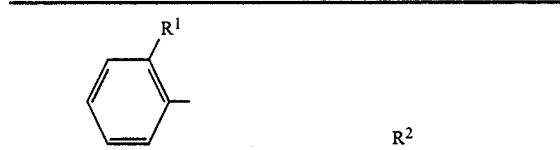
| R² | |
|---|---|
| 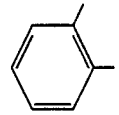 | 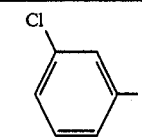 |
| 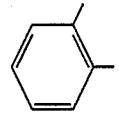 | 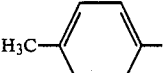 |
| 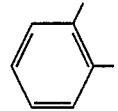 | 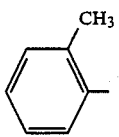 |
| 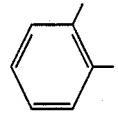 | 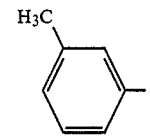 |
| 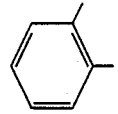 | 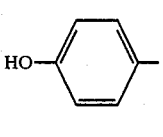 |
| 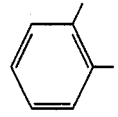 | 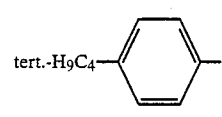 |
| 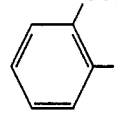 | 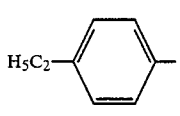 |
| 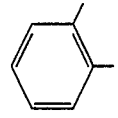 | 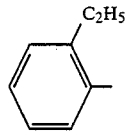 |
| 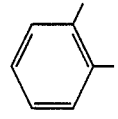 | 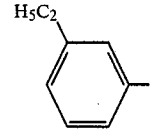 |
| 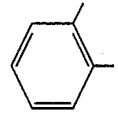 | 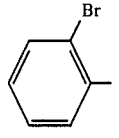 |
TABLE 1-continued
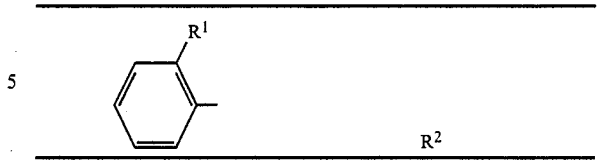
| R² | |
|---|---|
| 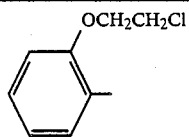 | 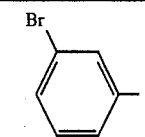 |
| 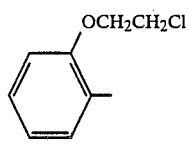 | 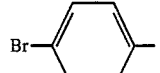 |
| 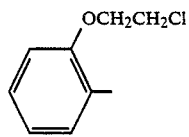 | 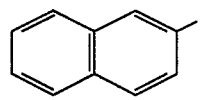 |
| 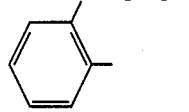 | 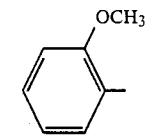 |
| 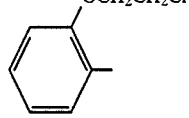 | 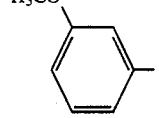 |
| 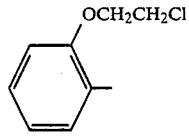 | 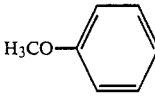 |
| 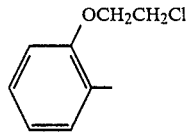 | 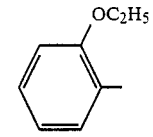 |
| 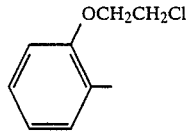 | 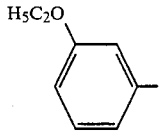 |
| 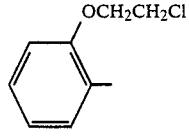 | 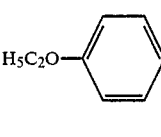 |
| 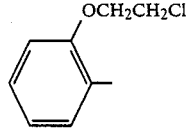 | 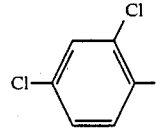 |

TABLE 1-continued

| R¹ (phenyl with substituent) | R² (phenyl with substituent) |
|---|---|
| 2-OCH₂CH₂Cl-phenyl | 2,4-diCl-phenyl |
| 2-OCH₂CH₂Cl-phenyl | 2-OC₃H₇-n-phenyl |
| 2-OCH₂CH₂Cl-phenyl | 3-n-H₇C₃O-phenyl |
| 2-OCH₂CH₂Cl-phenyl | 4-n-H₇C₃O-phenyl |
| 2-OCH₂CH₂Cl-phenyl | 4-H₃CS-phenyl |
| 2-OCH₂CH₂Cl-phenyl | 3-N(CH₃)₂-phenyl |
| 2-OCH₂CH₂Cl-phenyl | 2-F-phenyl |
| 2-OCH₂CH₂Cl-phenyl | 4-F-phenyl |
| 2-OCH₂CH₂Cl-phenyl | 4-(phenoxy)-phenyl |
| 2-Br-phenyl | 4-H₃C-phenyl |
| 2-Br-phenyl | 2-Cl-phenyl |
| 2-Br-phenyl | 3-H₃CO-phenyl |
| 2-Br-phenyl | 4-HO-phenyl |
| 2-Br-phenyl | phenyl |
| 2-OCH₃-phenyl | 2-Cl-phenyl |
| 2-OCH₃-phenyl | 3-H₃CO-phenyl |
| 2-F-phenyl | 4-H₃C-phenyl |
| 2-F-phenyl | 2-Cl-phenyl |
| 2-F-phenyl | 3-H₃CO-phenyl |
| 2-F-phenyl | 4-HO-phenyl |

TABLE 1-continued

Formula (III) provides a general definition of the 2-amino-triazines also to be used as starting substances in the process according to the invention. In this formula (III), $R^3$ and $R^4$ preferably represent those radicals which have already been mentioned as preferred for these substituents in connection with the description of the substances of the formula (I) according to the invention.

Examples which may be mentioned of the 2-aminotriazines of the formula (III) are:

TABLE 2

$$\text{H}_2\text{N}-\underset{N=\underset{R^4}{\overset{}{\Vert}}}{\overset{N-\underset{R^3}{\overset{}{\Vert}}}{\Vert}} \quad (III)$$

| R³ | R⁴ |
|---|---|
| CH₃ | CH₃ |
| OCH₃ | OCH₃ |
| CH₃ | OCH₃ |
| C₂H₅ | C₂H₅ |
| OC₂H₅ | OC₂H₅ |
| OC₂H₅ | CH₃ |
| OC₂H₅ | OCH₃ |
| CH₃ | SCH₃ |
| CH₃ | SC₂H₅ |
| OCH₃ | SCH₃ |
| OC₂H₅ | SCH₃ |
| OCH₃ | SC₂H₅ |
| OC₂H₅ | SC₂H₅ |
| CH₃ | NHCH₃ |
| CH₃ | N(CH₃)₂ |
| CH₃ | NHC₂H₅ |
| CH₃ | N(C₂H₅)₂ |
| OCH₃ | NHCH₃ |
| OCH₃ | NHC₂H₅ |
| OCH₃ | N(CH₃)₂ |
| OCH₃ | N(C₂H₅)₂ |
| OC₂H₅ | N(C₂H₅)₂ |
| OC₂H₅ | N(CH₃)₂ |
| SCH₃ | NHCH₃ |
| SCH₃ | N(CH₃)₂ |
| SCH₃ | NHC₂H₅ |
| SCH₃ | N(C₂H₅)₂ |
| SC₂H₅ | NHCH₃ |
| SC₂H₅ | N(CH₃)₂ |
| OC₂H₅ | NHCH₃ |
| OC₂H₅ | NHC₂H₅ |
| SC₂H₅ | N(C₂H₅)₂ |
| Cl | CH₃ |
| Cl | OCH₃ |

The 2-aminotriazines of the formula (III) are known and/or can be prepared by processes which are known per se.

The process according to the invention for the preparation of the new compounds of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl iospropyl ketone and methyl isobutyl ketone, esters, such as methyl and ethyl acetate, nitriles, such as, for example, acetonitrile and propionitrile, amides, such as, for example, dimethylformamide, dimethylacetamide and M-methyl-pyrrollidone, and dimethylsulphoxide, tetramethylene sulphone and hexamethylphosphoric acid triamide.

Acid acceptors which are used in the process according to the invention for the preparation of the new compounds of the formula (I) are all the acid-binding agents which can usually be employed for such reactions. Preferred possible acid-binding agents are alkali metal hydroxides, such as, for example, sodium and potassium hydroxide, alkali metal hydrides, such as, for example, sodium hydride, alkaline earth metal hydroxides, such as, for example, calcium hydroxide, and alkali metal carbonates and alcoholates, such as sodium and potassium carbonate, sodium and potassium methylate or ethylate or potassium tert.-butylate.

The reactions are in general carried out at temperatures between −20° C. and 150° C., preferably at temperatures between 0° C. and 80° C. The reactions are in general carried out under normal pressure.

For carrying out the process according to the invention, the starting substances of the formulae (II) and (III) and if appropriate the suitable acid acceptor are employed in equimolar amounts.

Preferably, a compound of the formula (III), the acid acceptor and the diluent, such as, for example, tetrahydrofuran, are initially taken and are stirred for some hours. The compound of the formula (II) is then added. After the reaction, the reaction solution is concentrated, water is added, the mixture is filtered with suction over silica gel and the filtrate is rendered weakly acid with a mineral acid, such as, for example, hydrochloric acid. The solution is taken up in an organic diluent, such as, for example, methylene chloride. The organic phase is washed with saturated sodium carbonate solution and then with water, dried and concentrated. The crude products are purified by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner in other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating dicotyledon weeds in monocotyledon crops, such as, for example, barley and wheat, by the post- and pre-emergence process.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins. clays, talc, chalk, quartz, attapulgite, montmorillonite or diatomaceous earth, and ground synthetic minerals, such as highly disperse silicic acid, alumina and silicates, as solid carriers for granules there are suitable: for example, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 2-chloro-N-{[(4-methoxy-6-methyl-1,3,5-triazin-2-yl)-amino]-carbonyl}-benzenesulphonamide, 2-ethylamino-6-(1,1-dimethylethyl-amino)-4-methylthio-1,3,5-triazine, methyl 3-(2,4-dichlorophenoxy)-6-nitro-benzoate, methyl 2-[4-(2,4-dichlorophenoxy)-phenoxy]-propionate, the R-enantiomer of (trimethylsilyl)-methyl 2-{4-[(3,5-dichloro-2-pyridinyl)-oxy]-phenoxy}-propionate, 2,4-dichlorophenoxyacetic acid, 2-(2,4-dichlorophenoxy)-propionic acid, 4-chloro-2-methyl-phenoxy-acetic acid, 2-(4-chloro-2-methyl-phenoxy)-propionic acid 3,5-diiodo-4-hydroxybenzonitrile, 3,5-dibromo-4-hydroxy-benzonitrile, N-(1-ethylpropyl)-3,4-dimethyl-2,6-dinitroaniline, 2,3,3-trichloroallyl N,N-diisopropyl-thiolcarbamate, 2-(2-benzothiazolyloxy)-N-methyl-N-phenylacetamide, methyl 2-[4,5-dihydro-4-methyl-4-(1-methylethyl)-5-oxo-1H-imidazol-2-yl]-4(5)-methyl-benzoate, [(4-amino-3,5-dichloro-6-fluoro-2-pyridyl)-oxy]-acetic acid and 3-isopropyl-2,1,3-benzothiadiazin-4-one 2,2-dioxide. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

The active compounds according to the invention in some cases also have a fungicidal activity, in particular against *Pyricularia oryzae* on rice.

PREPARATION EXAMPLES

Example 1

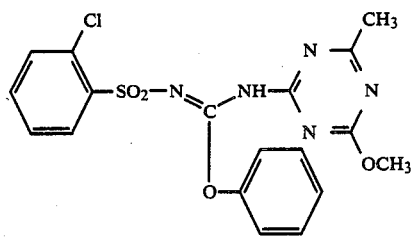

7 g (0.05 mol) of 2-amino-4-methoxy-6-methyl-1,3,5-triazine are dissolved in 100 ml of tetrahydrofuran, and 5.9 g (0.05 mol) of potassium tert.-butylate are added at 20° C. After 2 hours, 19.4 g (0.05 mol) of O,O-diphenyl N-(2-chlorobenzenesulphonyl)-iminocarbonate are added at 20° C.; the mixture is then subsequently stirred at 20° C. for 16 hours. The reaction mixture is then poured onto 500 ml of water and filtered. The filtrate is rendered weakly acid with 2N hydrochloric acid and extracted with methylene chloride. The organic phase is washed neutral, dried and concentrated. The residue is stirred with a mixture of isopropanol/diisopropyl ether, filtered off with suction, washed and dried.

15.5 g (71.8% of theory) of N'-(2-chloro-benzenesulphonyl)-N''-(4-methoxy-6-methyl-1,3,5-triazin-2-yl)-O-phenyl-isourea of melting point 95° C. are obtained.

Example 2

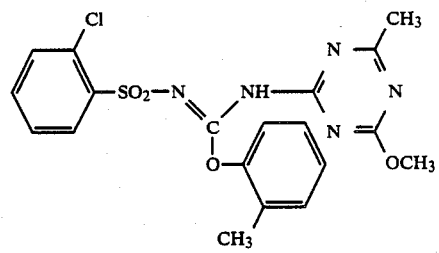

A mixture of 5.6 g (0.04 mol) of 2-amino-4-methoxy-6-methyl-1,3,5-triazine, 2.7 g (0.08 mol) of sodium hydride in paraffin and 100 ml of tetrahydrofuran is stirred at 25° C. for 15 hours. 16.6 g (0.04 mol) of O,O-di-(4-methyl-phenyl) 2-chlorobenzenesulphonyl-iminocarbonate are then added to this mixture in portions so that a temperature of 30° C. is not exceeded; the mixture is then subsequently stirred at 25° C. for 3 hours. 300 ml of water are added to the reaction mixture, while cooling with ice, and the aqueous phase is brought to a pH of about 5 with dilute hydrochloric acid. The aqueous phase is extracted twice with 100 ml of methylene chloride each time and the combined methylene chloride phases are washed with water and, after drying over sodium sulphate, are concentrated. After incipient distillation (bath temperature/pressure: 140° C./202 Pa), the residue is triturated with ethanol, filtered off and dried.

5.1 g (29.5% of theory) of N'-(2-chlorobenzene-sulphonyl)-N''-(4-methoxy-6-methyl-1,3,5-triazin-2-yl)O-(2-methyl-phenyl)-isourea are obtained in the form of colorless crystals of melting point 118° C.

The following compounds of the formula (I) can be prepared analogously to Example 1 and 2:

TABLE 3

| Example No. | R¹ | R² | R³ | R⁴ | Melting point [°C.] |
|---|---|---|---|---|---|
| 3 | Cl | O₂N—C₆H₄— | OCH₃ | OCH₃ | 125 |
| 4 | Cl | O₂N—C₆H₄— | CH₃ | OCH₃ | 165 |

TABLE 3-continued $$\text{(I)}$$

Structure (I): 2-R¹-phenyl-SO₂-N=C(OR²)-NH-C(=N-)(R³)-N=C(R⁴)-N= (1,3,5-triazine)

| Example No. | R¹ (2-substituted phenyl) | R² | R³ | R⁴ | Melting point [°C] |
|---|---|---|---|---|---|
| 5 | 2-Cl-phenyl | 3-NO₂-phenyl | CH₃ | OCH₃ | 152 |
| 6 | 2-Cl-phenyl | phenyl | CH₃ | N(CH₃)₂ | 128 |
| 7 | 2-Cl-phenyl | phenyl | CH₃ | SCH₃ | 135 |
| 8 | 2-OCH₃-phenyl | 3-NO₂-phenyl | OCH₃ | OCH₃ | 175 |
| 9 | 2-OCH₃-phenyl | phenyl | OCH₃ | OCH₃ | 176 |
| 10 | 2-Cl-phenyl | phenyl | OCH₃ | OCH₃ | 96 |
| 11 | 2-Cl-phenyl | 3-CH₃-phenyl | CH₃ | OCH₃ | 141 |
| 12 | 2-Cl-phenyl | 4-CH₃-phenyl | CH₃ | OCH₃ | 114 |
| 13 | 2-Cl-phenyl | 4-CH₃O-phenyl | CH₃ | OCH₃ | |

TABLE 3-continued

Structure (I):

2-R¹-C₆H₄-SO₂-N=C(OR²)-NH-[triazine with R³ and R⁴]

| Example No. | R¹ (2-substituted phenyl) | R² | R³ | R⁴ | Melting point [°C.] |
|---|---|---|---|---|---|
| 14 | 2-Br-C₆H₄- | C₆H₅- | CH₃ | OCH₃ | 144 |
| 15 | 2-Br-C₆H₄- | C₆H₅- | OCH₃ | OCH₃ | |
| 16 | 2-Br-C₆H₄- | C₆H₅- | CH₃ | CH₃ | |
| 17 | 2-Br-C₆H₄- | 4-CH₃-C₆H₄- | CH₃ | OCH₃ | 152 |
| 18 | 2-Br-C₆H₄- | 3-CH₃-C₆H₄- | CH₃ | OCH₃ | 158 |
| 19 | 2-Br-C₆H₄- | 4-t-C₄H₉-C₆H₄- | CH₃ | CH₃ | |
| 20 | 2-Cl-C₆H₄- | 4-t-C₄H₉-C₆H₄- | CH₃ | OCH₃ | |
| 21 | 2-F-C₆H₄- | C₆H₅- | CH₃ | OCH₃ | |
| 22 | 2-F-C₆H₄- | C₆H₅- | OCH₃ | OCH₃ | |

TABLE 3-continued $$\underset{OR^2}{\overset{R^1}{\underset{}{\bigcirc}}} -SO_2-N=\underset{OR^2}{\overset{}{C}}-NH-\underset{N=}{\overset{N=}{\underset{}{\bigcirc}}}\overset{R^3}{\underset{R^4}{}} \quad (I)$$

| Example No. | R¹ (aryl) | R² | R³ | R⁴ | Melting point [°C.] |
|---|---|---|---|---|---|
| 23 | 2-F-phenyl | phenyl | CH₃ | CH₃ | |
| 24 | 2-F-phenyl | CH₃ / 3-CH₃-phenyl | CH₃ | OCH₃ | |
| 25 | 2-F-phenyl | 4-CH₃O-phenyl | CH₃ | OCH₃ | 107 |
| 26 | 2-CF₃-phenyl | phenyl | CH₃ | OCH₃ | |
| 27 | 2-CF₃-phenyl | phenyl | OCH₃ | OCH₃ | 103 |
| 28 | 2-CF₃-phenyl | phenyl | CH₃ | CH₃ | |
| 29 | 2-CF₃-phenyl | 4-CH₃-phenyl | CH₃ | OCH₃ | |
| 30 | 2-CF₃-phenyl | 4-CH₃O-phenyl | CH₃ | OCH₃ | |
| 31 | 2-OCH₃-phenyl | phenyl | CH₃ | CH₃ | 153 |

TABLE 3-continued

Structure (I): 2-R¹-C₆H₄-SO₂-N=C(OR²)-NH-C(=N-)(triazine with R³, R⁴)

| Example No. | R¹ | R² | R³ | R⁴ | Melting point [°C.] |
|---|---|---|---|---|---|
| 32 | 2-OCH₃-C₆H₄- | C₆H₅- | CH₃ | OCH₃ | 118 |
| 33 | 2-CN-C₆H₄- | C₆H₅- | CH₃ | CH₃ | |
| 34 | 2-CN-C₆H₄- | C₆H₅- | CH₃ | OCH₃ | |
| 35 | 2-CN-C₆H₄- | C₆H₅- | OCH₃ | OCH₃ | |
| 36 | 2-C₆H₅-C₆H₄- | 4-CH₃-C₆H₄- | OCH₃ | OCH₃ | 139 |
| 37 | 2-Cl-C₆H₄- | 4-(CH₃S)-C₆H₄- | OCH₃ | OCH₃ | 124 |
| 38 | 2-CF₃-C₆H₄- | 2,6-(CH₃)₂-C₆H₃- | CH₃ | SCH₃ | 123 |
| 39 | 2-CF₃-C₆H₄- | C₆H₅- | CH₃ | SCH₃ | 95 |

TABLE 3-continued

Structure (I):

Ar(R¹)-SO₂-N=C(OR²)-NH-[triazine with R³, R⁴]

| Example No. | R¹ (phenyl substituent) | R² | R³ | R⁴ | Melting point [°C.] |
|---|---|---|---|---|---|
| 40 | 2-OCH₃-phenyl | phenyl | CH₃ | SCH₃ | 120 |
| 41 | 2-OCH₃-phenyl | phenyl | CH₃ | N(CH₃)₂ | 151 |
| 42 | 2-CF₃-phenyl | 2,3-dimethylphenyl | OCH₃ | OCH₃ | 128 |
| 43 | 2-OCH₃-phenyl | 2,3-dimethylphenyl | OCH₃ | OCH₃ | 123 |
| 44 | 2-CF₃-phenyl | 2,3-dimethylphenyl | CH₃ | N(CH₃)₂ | 143 |
| 45 | 2-OCH₃-phenyl | 2-methyl-3-chlorophenyl | CH₃ | SCH₃ | 127 |
| 46 | 2-CF₃-phenyl | 2,3-dimethylphenyl | CH₃ | OCH₃ | 128 |
| 47 | 2-OCH₃-phenyl | 2-methyl-3-chlorophenyl | CH₃ | OCH₃ | 131 |

TABLE 3-continued (I)

Structure: Ar(R¹)-SO₂-N=C(OR²)-NH-[triazine with R³, R⁴]

| Example No. | R¹ (on phenyl) | R² | R³ | R⁴ | Melting point [°C.] |
|---|---|---|---|---|---|
| 48 | 2-OCH₃-phenyl | 3-methyl-4-chlorophenyl | CH₃ | N(CH₃)₂ | 147 |
| 49 | 2-OCH₃-phenyl | phenyl | CH₃ | N(CH₃)₂ | 162 |
| 50 | 2-F-phenyl | 2-methylphenyl | CH₃ | OCH₃ | 94 |
| 51 | 2-F-phenyl | 4-methylphenyl | CH₃ | OCH₃ | 108 |
| 52 | 2-Br-phenyl | 2-methylphenyl | CH₃ | OCH₃ | 147 |
| 53 | 2-Br-phenyl | 4-methoxyphenyl | CH₃ | OCH₃ | 132 |

Starting compounds of the formula (II)

Example (II-1)

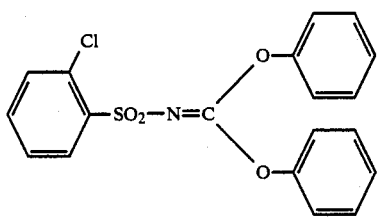

23.2 g (0.085 mol) of 2-chlorobenzenesulphonyl isocyanide dichloride are dissolved in 100 ml of acetone, and 19.7 g (0.085 mol) of sodium phenolate are added in portions at 20° C. The reaction mixture is subsequently stirred at 20° C. for 16 hours and filtered with suction over kieselguhr, and the filtrate is concentrated in vacuo. The residue is triturated with isopropanol, filtered off with suction, washed and dried.

29.4 g (89% of theory) of O,O-diphenyl 2-chlorobenzenesulphonyliminocarbonate of melting point 130° C. are obtained.

Example (II-2)

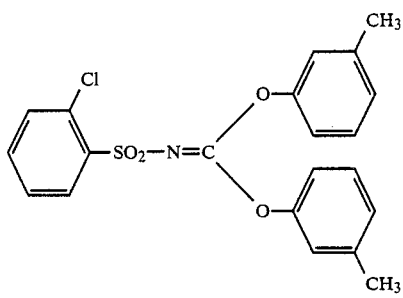

22.6 g (0.217 mol) of triethylamine are added dropwise to a mixture of 27.2 g (0.1 mol) of 2-chlorobenzenesulphonyl isocyanide dichloride, 21.6 g (0.2 mol) of 3-methylphenol and 150 ml of toluene such that a reaction temperature of 40° C. is not exceeded. The reaction mixture is then subsequently stirred at 25° C. for 3 hours and filtered with suction. The filtrate is extracted with 200 ml of methylene chloride and the organic phase is washed with water, dried over sodium sulphate and concentrated.

24.8 g (59.7% of theory) of O,O-di-(3-methylphenyl) 2-chlorobenzenesulphonyliminocarbonate are obtained in the form of colorless crystals of melting point 98° C.

The following compounds of the formula (II) can be prepared analogously to Example (II-1) and (II-2):

TABLE 4

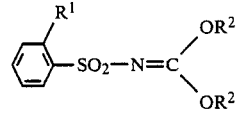
(II)

| Example No. | R¹ (on 2-position of phenyl) | R² | Physical constants |
|---|---|---|---|
| II-3 | Cl | 4-O₂N-C₆H₄- | Melting point 183° C. |
| II-4 | OCH₂CH₂Cl | C₆H₅- | |
| II-5 | F | C₆H₅- | Melting point 117° C. |
| II-6 | Br | C₆H₅- | |
| II-7 | CN | C₆H₅- | |
| II-8 | OCH₃ | C₆H₅- | Melting point 170° C. |
| II-9 | CF₃ | C₆H₅- | |
| II-10 | CH₃ | C₆H₅- | |
| II-11 | OCH₂CH₂Cl | 4-HO-C₆H₄- | |
| II-12 | F | 4-HO-C₆H₄- | |
| II-13 | Br | 4-HO-C₆H₄- | |
| II-14 | CN | 4-HO-C₆H₄- | |
| II-15 | OCH₃ | 4-HO-C₆H₄- | |
| II-16 | CF₃ | 4-HO-C₆H₄- | |
| II-17 | Cl | 4-HO-C₆H₄- | |
| II-18 | CH₃ | 4-HO-C₆H₄- | |
| II-19 | F | 4-Br-C₆H₄- | |
| II-20 | Br | 4-Br-C₆H₄- | |
| II-21 | CN | 4-Br-C₆H₄- | |

TABLE 4-continued $$\underset{\underset{OR^2}{OR^2}}{R^1} \quad (II)$$

| Example No. | R¹ | R² | Physical constants |
|---|---|---|---|
| II-22 | 2-OCH₃-C₆H₄ | 4-Br-C₆H₄ | |
| II-23 | 2-CF₃-C₆H₄ | 4-Br-C₆H₄ | |
| II-24 | 2-Cl-C₆H₄ | 4-Br-C₆H₄ | |
| II-25 | 2-CH₃-C₆H₄ | 4-Br-C₆H₄ | |
| II-26 | 2-F-C₆H₄ | 4-H₃CO-C₆H₄ | |
| II-27 | 2-Br-C₆H₄ | 4-H₃CO-C₆H₄ | |
| II-28 | 2-CN-C₆H₄ | 4-H₃CO-C₆H₄ | |
| II-29 | 2-OCH₃-C₆H₄ | 4-H₃CO-C₆H₄ | |
| II-30 | 2-CF₃-C₆H₄ | 4-H₃CO-C₆H₄ | |
| II-31 | 2-Cl-C₆H₄ | 4-H₃CO-C₆H₄ | |
| II-32 | 2-CH₃-C₆H₄ | 4-H₃CO-C₆H₄ | |
| II-33 | 2-F-C₆H₄ | 4-Cl-C₆H₄ | |
| II-34 | 2-Br-C₆H₄ | 4-Cl-C₆H₄ | |
| II-35 | 2-CN-C₆H₄ | 4-Cl-C₆H₄ | |
| II-36 | 2-OCH₃-C₆H₄ | 4-Cl-C₆H₄ | |
| II-37 | 2-CF₃-C₆H₄ | 4-Cl-C₆H₄ | |
| II-38 | 2-Cl-C₆H₄ | 4-Cl-C₆H₄ | |
| II-39 | 2-CH₃-C₆H₄ | 4-Cl-C₆H₄ | |
| II-40 | 2-F-C₆H₄ | 4-H₃CS-C₆H₄ | |
| II-41 | 2-Br-C₆H₄ | 4-H₃CS-C₆H₄ | |
| II-42 | 2-CN-C₆H₄ | 4-H₃CS-C₆H₄ | |
| II-43 | 2-OCH₃-C₆H₄ | 4-H₃CS-C₆H₄ | |
| II-44 | 2-CF₃-C₆H₄ | 4-H₃CS-C₆H₄ | |
| II-45 | 2-Cl-C₆H₄ | 4-H₃CS-C₆H₄ | |
| II-46 | 2-CH₃-C₆H₄ | 4-H₃CS-C₆H₄ | |
| II-47 | 2-F-C₆H₄ | 4-H₃C-C₆H₄ | |

Example (II-2)

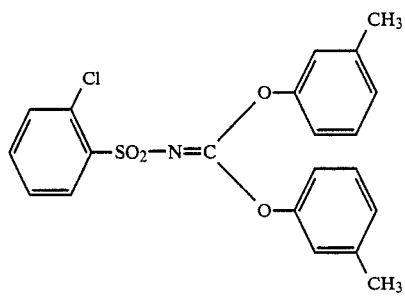

22.6 g (0.217 mol) of triethylamine are added dropwise to a mixture of 27.2 g (0.1 mol) of 2-chlorobenzenesulphonyl isocyanide dichloride, 21.6 g (0.2 mol) of 3-methylphenol and 150 ml of toluene such that a reaction temperature of 40° C. is not exceeded. The reaction mixture is then subsequently stirred at 25° C. for 3 hours and filtered with suction. The filtrate is extracted with 200 ml of methylene chloride and the organic phase is washed with water, dried over sodium sulphate and concentrated.

24.8 g (59.7% of theory) of O,O-di-(3-methylphenyl) 2-chlorobenzenesulphonyliminocarbonate are obtained in the form of colorless crystals of melting point 98° C.

The following compounds of the formula (II) can be prepared analogously to Example (II-1) and (II-2):

TABLE 4

$$\underset{\text{(II)}}{\text{Ar-SO}_2-\text{N}=\text{C}(\text{OR}^2)_2}$$ where Ar = 2-R¹-phenyl

| Example No. | R¹ (on 2-position of phenyl) | R² | Physical constants |
|---|---|---|---|
| II-3 | Cl | 4-O₂N-C₆H₄- | Melting point 183° C. |
| II-4 | OCH₂CH₂Cl | C₆H₅- | |
| II-5 | F | C₆H₅- | Melting point 117° C. |
| II-6 | Br | C₆H₅- | |
| II-7 | CN | C₆H₅- | |
| II-8 | OCH₃ | C₆H₅- | Melting point 170° C. |
| II-9 | CF₃ | C₆H₅- | |
| II-10 | CH₃ | C₆H₅- | |
| II-11 | OCH₂CH₂Cl | 4-HO-C₆H₄- | |
| II-12 | F | 4-HO-C₆H₄- | |
| II-13 | Br | 4-HO-C₆H₄- | |
| II-14 | CN | 4-HO-C₆H₄- | |
| II-15 | OCH₃ | 4-HO-C₆H₄- | |
| II-16 | CF₃ | 4-HO-C₆H₄- | |
| II-17 | Cl | 4-HO-C₆H₄- | |
| II-18 | CH₃ | 4-HO-C₆H₄- | |
| II-19 | F | 4-Br-C₆H₄- | |
| II-20 | Br | 4-Br-C₆H₄- | |
| II-21 | CN | 4-Br-C₆H₄- | |

TABLE 4-continued $$\underset{\substack{R^1\\\text{(o-C}_6\text{H}_4\text{)}}}{}\text{SO}_2-N=C\underset{OR^2}{\overset{OR^2}{}}\quad(II)$$

Phenyl ring bears R¹ at ortho position.

| Example No. | R¹ (on o-phenyl) | R² (aryl) | Physical constants |
|---|---|---|---|
| II-22 | OCH₃ | 4-Br-C₆H₄ | |
| II-23 | CF₃ | 4-Br-C₆H₄ | |
| II-24 | Cl | 4-Br-C₆H₄ | |
| II-25 | CH₃ | 4-Br-C₆H₄ | |
| II-26 | F | 4-CH₃O-C₆H₄ | |
| II-27 | Br | 4-CH₃O-C₆H₄ | |
| II-28 | CN | 4-CH₃O-C₆H₄ | |
| II-29 | OCH₃ | 4-CH₃O-C₆H₄ | |
| II-30 | CF₃ | 4-CH₃O-C₆H₄ | |
| II-31 | Cl | 4-CH₃O-C₆H₄ | |
| II-32 | CH₃ | 4-CH₃O-C₆H₄ | |
| II-33 | F | 4-Cl-C₆H₄ | |
| II-34 | Br | 4-Cl-C₆H₄ | |
| II-35 | CN | 4-Cl-C₆H₄ | |
| II-36 | OCH₃ | 4-Cl-C₆H₄ | |
| II-37 | CF₃ | 4-Cl-C₆H₄ | |
| II-38 | Cl | 4-Cl-C₆H₄ | |
| II-39 | CH₃ | 4-Cl-C₆H₄ | |
| II-40 | F | 4-CH₃S-C₆H₄ | |
| II-41 | Br | 4-CH₃S-C₆H₄ | |
| II-42 | CN | 4-CH₃S-C₆H₄ | |
| II-43 | OCH₃ | 4-CH₃S-C₆H₄ | |
| II-44 | CF₃ | 4-CH₃S-C₆H₄ | |
| II-45 | Cl | 4-CH₃S-C₆H₄ | |
| II-46 | CH₃ | 4-CH₃S-C₆H₄ | |
| II-47 | F | 4-CH₃-C₆H₄ | |

TABLE 4-continued $$\text{R}^1\text{-C}_6\text{H}_4\text{-SO}_2\text{-N=C(OR}^2\text{)}_2 \quad (II)$$

| Example No. | R¹ (on phenyl) | R² | Physical constants |
|---|---|---|---|
| II-109 | Cl | -C₆H₄-OCH₃ | |
| II-110 | OCH₃ | -C₆H₄-OCH₃ | |
| II-111 | CH₃ | -C₆H₄-OCH₃ | |
| II-112 | CF₃ | -C₆H₄-OCH₃ | |
| II-113 | Cl | -C₆H₄-OCH₃ | |
| II-114 | OCH₃ | -C₆H₄-C₂H₅ | |
| II-115 | CH₃ | -C₆H₄-C₂H₅ | |
| II-116 | CF₃ | -C₆H₄-C₂H₅ | |
| II-117 | Cl | -C₆H₄-C₂H₅ | |
| II-118 | OCH₃ | -C₆H₄-C₂H₅ | |
| II-119 | CH₃ | -C₆H₄-C₂H₅ | |
| II-120 | CF₃ | -C₆H₄-C₂H₅ | |
| II-121 | Cl | -C₆H₄-C₂H₅ | |
| II-122 | OCH₃ | -C₆H₄-NO₂ | |
| II-123 | F | -C₆H₄-CH₃ | |
| II-124 | Br | -C₆H₄-CH₃ | |
| II-125 | Br | t-H₉C₄-C₆H₄- | |

Starting compounds of the formula (IV)

Example (IV-1)

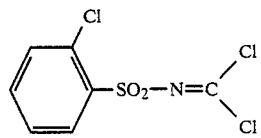

30 g (0.1 mol) of S,S-dimethyl 2-chlorobenzenesulphonyliminodithiocarbonate are dissolved in 200 ml of carbon tetrachloride, and 71 g (1 mol) of dry chlorine gas are passed in at 20° C. Thereafter, the mixture is subsequently stirred for 30 minutes and concentrated in vacuo. The residue is poured into petroleum ether and the product which has precipitated is filtered off with suction and dried.

23.3 g (86% of theory) of 2-chlorobenzenesulphonylisocyanide dichloride of melting point 74° C. are obtained.

The compound (IV-1) can also be prepared as follows:

A solution of 88.7 g (0.3 mol) of S,S-dimethyl 2-chlorobenzenesulphonyliminodithiocarbonate in 200 ml of chloroform is heated to 60° C. and 300 g (2.1 mol) of sulphuryl chloride are added dropwise at this temperature. The mixture is subsequently stirred at 60° C. for one hour until the evolution of gas has ended. It is then concentrated and the residue is subjected to incipient distillation (bath temperature/pressure: 50° C./200 Pa). The residue is triturated with petroleum ether, filtered off with suction and dried.

64 g (78% of theory) of 2-chlorobenzenesulphonyl isocyanide dichloride of melting point 82° C. are obtained.

The following compounds of the formula (IV) can be prepared analogously to Example (IV-1):

TABLE 5

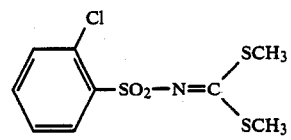

(IV)

| Example No. | R¹ | Physical constants |
|---|---|---|
| IV-2 | CH₃ | |
| IV-3 | OCH₂CH₂Cl | |
| IV-4 | OC₂H₅ | |
| IV-5 | F | Boiling point 130° C./600 Pa |
| IV-6 | Br | Melting point 107° C. (decomposition) |
| IV-7 | CN | |
| IV-8 | OCH₃ | Oil |
| IV-9 | CF₃ | |

Starting compounds of the formula (VI)

Example (VI-1)

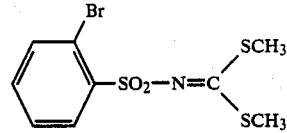

8 g (0.2 mol) of sodium hydroxide—dissolved in 15 ml of water—and 6 ml (0.11 mol) of carbon disulphide are simultaneously added dropwise (from different dropping funnels) to a solution of 20 g (0.1 mol) of 2-chlorobenzenesulphonamide in 80 ml of dimethylformamide at 20° C. After the mixture has been stirred for one hour, 13 ml (0.22 mol) of methylene chloride are added dropwise and the reaction mixture is stirred at 20° C. for a further hour. The product is precipitated by addition of 500 ml of water and isolated by filtration with suction.

22.1 g (75% of theory) of S,S-dimethyl 2-chlorobenzenesulphonyliminodithiocarbonate of melting point 112° C. are thus obtained.

Example (VI-2)

A mixture of 236 g (1 mol) of 2-bromo-benzenesulphonamide, 1,500 ml of dimethylformamide and 85 g (1.11 mols) of carbon disulphide is cooled to 5° C. and a solution of 80 g (2 mols) of sodium hydroxide in 150 ml of water is added dropwise so that a reaction temperature of 10° C. is not exceeded. The reaction mixture is subsequently stirred at 5° C.–10° C. for a further 30 minutes, 284 g (2 mols) of methyl iodide are added dropwise at this temperature and the mixture is subsequently stirred at 20° C.–25° C. for 18 hours. The reaction mixture is poured into 5 l of water and the reaction product which has precipitated is filtered off. The residue on the filter is taken up in 1.5 l of methylene chloride and the methylene chloride phase is filtered, dried over sodium sulphate and concentrated. The residue is triturated with 1 l of petroleum ether.

290 g (85% of theory) of S,S-dimethyl 2-bromobenzenesulphonyliminodithiocarbonate of melting point 143° C. are obtained.

The compounds of the formula (VI) listed in the following Table 6 can be prepared analogously to Example (VI-1) and (VI-2):

TABLE 6

(VI)

| Example No. | R¹ | Melting point/ [°C] |
|---|---|---|
| VI-3 | CN | |
| VI-4 | F | 104 |
| VI-5 | OCH₃ | 112 |

TABLE 6-continued

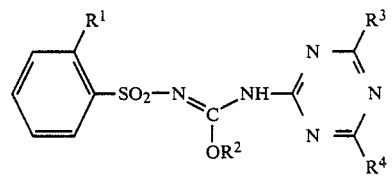

| Example No. | $R^1$ | Melting point/ [°C] |
|---|---|---|
| VI-6 | $CF_3$ | 124 |

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compounds applied per unit area being decisive. After three weeks, the degree of damage to the plants is rated in % damage in comparison to the development of the untreated control. The figures denote:

0% = no action (like untreated control)
100% = total destruction

In this test, for example, the compounds of preparation Examples (1) and (10) exhibit a better action than comparison substance (A) in combating ditotyledon weeds, such as, for example, Datura, Galium, Ipomoea, Sinapis and Viola, in crops such as barley and wheat.
(A) = N'-(2-chloro-benzenesulphonyl)-N''-(4,6-dimethyl-1,3,5-triazin-2-yl)-O-phenyl-isourea (known from European Pat. No. A-173,957).

Example B

Post-emergence test
Solvent: 5 parts by weight of acetone
Emulsifier: 1 part by weight of alkylarlyl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds of preparation Examples (1) and (10) exhibit a better action than the comparison substance (A) in combating dicotyledon weeds, such as Cassia, Galium, Matricaria and Stellaria, in crops such as barley and wheat.

It will be understood that the specification and examples are illustrative but not limitative of the present invention and that other embodiments within the spirit and scope of the invention will suggest themselves to those skilled in the art.

We claim:

1. A phenylsulphonylisourea of the formula in which
$R^1$ represents flourine, chlorine, bromine, cyano or $C_1$–$C_4$-alkyl (which is optionally substituted by fluorine, chlorine, bromine, cyano, $C_1$–$C_2$-alkoxy or phenyl) or represents $C_1$–$C_2$-alkoxy (which is optionally substituted by chlorine, bromine, cyano or $C_1$–$C_2$-alkoxy),
$R^2$ represents an optionally substituted phenyl or naphthyl radical, the optional substituents of the phenyl radical being one or more radicals from the group consisting of halogen, cyano, nitro, hydroxyl, carboxyl, $C_1$–$C_6$-alkyl (which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl), $C_3$–$C_6$-cycloalkyl, $C_1$–$C_4$-alkoxy (which is optionally substituted by fluorine, chlorine, bromine, cyano, carboxyl, $C_1$–$C_4$-alkoxy, $C_1$–$C_4$-alkylthio or $C_1$–$C_4$-alkoxy-carbonyl), $C_1$–$C_4$-aklylthio (which is optionally substituted by fluorine, chlorine, bromine, cyano, carboxyl or $C_1$–$C_4$-alkoxy-carbonyl), amino, $C_1$–$C_4$-alkyl-amino and di-($C_1$–$C_4$-alkyl)-amino (which are optionally substituted by fluorine, chlorine, bromine, cyano, carboxyl, $C_1$–$C_4$-alkoxy or $C_1$–$C_4$-alkoxy-carbonyl), $C_1$–$C_4$-alkyl-carbonyl-amino, $C_1$–$C_4$-alkoxy-carbonylamino, (di)-$C_1$–$C_4$-alkylamino-carbonylamino, formyl, $C_1$–$C_4$-alkyl-carbonyl, benzoyl, $C_1$–$C_4$-alkoxy-carbonyl, phenoxy-carbonyl, benzyloxycarbonyl, phenyl (which is optionally substituted by fluorine, chlorine, bromine, cyano, nitro, hydroxyl or methyl), phenoxy, phenylthio, phenylsulphonyl, phenylamino and phenylazo (which are optionally substituted by fluorine, chlorine, bromine, cyano, nitro, methyl and/or trifluoromethyl), pyridoxy and pyrimidoxy (which are optionally substituted by fluorine, chlorine, bromine, cyano, nitro, methyl and/or trifluoromethyl), $C_1$–$C_4$-alkyl-carbonyloxy, $C_1$–$C_4$-alkoxy-carbonyloxy, $C_1$–$C_4$-alkyl-aminocarbonyloxy and di-($C_1$–$C_4$-alkyl)-amino-carbonyloxy, the optional substituents on the naphthyl radical being fluorine, chlorine, bromine, cyano, nitro, methyl and/or triflouromethyl;
$R^3$ represents hydrogen, fluorine, chlorine, bromine, hydroxyl, $C_1$–$C_4$-alkylamino, di-($C_1$–$C_4$-alkyl)-amino, $C_1$–$C_4$-alkyl (which is optionally substituted by fluorine and/or chlorine), $C_1$–$C_4$-alkoxy (which is optionally substituted by fluorine and/or chlorine) or $C_1$-$C_4$-alkylthio (which is optionally substituted by fluorine and/or chlorine) and $R^4$ represents hydrogen, fluorine, chlorine, bromine, hydroxyl, $C_1$-$C_4$-alkoxy (which is optionally substituted by fluorine and/or chlorine), $C_1$-$C_4$-alkylthio (which is optionally substituted by fluorine and/or chlorine), $C_1$-$C_4$-alkylamino or di-($C_1$-$C_4$-alkyl)-amino.

2. A phenylsulphonylisourea of the formula

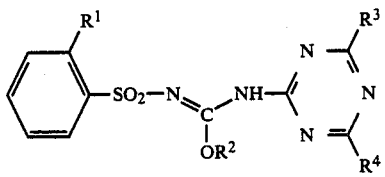

in which
  $R^1$ represents fluorine, chlorine, bromine, cyano, methyl, ethyl, trifluoromethyl, methoxy, 2-chloroethoxy or benzyl,
  $R^2$ represents a phenyl radical, which is optionally substituted by one or two radicals from the group consisting of fluorine, chlorine, bromine, iodine, cyano, nitro, hydroxyl, carboxyl, $C_1$-$C_3$-alkoxycarbonyl, $C_1$-$C_4$-alkyl, trifluoromethyl, hydroxymethyl, methoxycarbonylmethyl, phenyl-$C_1$-$C_3$-alkyl, cyclohexyl, $C_1$-$C_3$-alkoxy, trifluoromethoxy, $C_1$-$C_3$-alkylthio, trifluoromethylthio, dimethylamino, amino, acetylamino, methylaminocarbonyl, formyl, acetyl, benzoyl, phenyl, hydroxyphenyl, phenoxy (which is optionally substituted by chlorine and/or trifluoromethyl), phenylamino, phenylazo and pyridoxy (which is optionally substituted by chlorine and/or trifluoromethyl), or is a napththyl radical;
  $R^3$ represents fluorine, chlorine, methyl, ethyl, methoxy, ethoxy, methylthio, ethylthio, methylamino, ethylamino, dimethylamino or diethylamino, and
  $R^4$ represents fluorine, chlorine, methoxy, ethoxy, methylthio, ethylthio, methyl-amino, ethylamino, dimethylamino or diethylamino.

3. A compound according to claim 1, wherein such compound is N'-(2-chloro-benzene-sulphonyl)-N''-(4-methoxy-6-methyl-1,3,5-triazin-2-yl)-O-phenyl-isourea of the formula

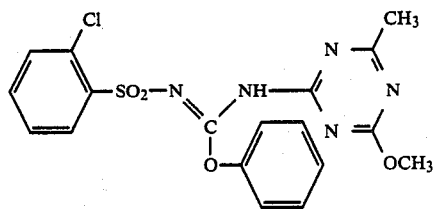

4. A compound according to claim 1, wherein such compound is N'-(2-chloro-benzene-sulphonyl)-N''-(4,6-dimethoxy-1,3,5-triazin-2-yl)-O-phenyl-isourea of the formula

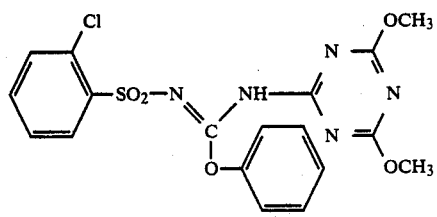

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is
  N'-(2-chloro-benzene-sulphonyl)-N''-(4-mehtoxy-6-methyl-1,3,5-triazin-2-yl)-O-phenyl-isourea or
  N'-(2-chloro-benzene-sulphonyl)-N''-(4,6-dimethoxy-1,3,5-triazin-2-yl)-O-phenyl-isourea.

* * * * *

UNITED STATES PATENT AND TRADEMARK OFFICE
CERTIFICATE OF CORRECTION

PATENT NO. : 4,846,879
DATED : July 11, 1989
INVENTOR(S) : Fest et al.

It is certified that error appears in the above-identified patent and that said Letters Patent is hereby corrected as shown below:

Col. 15, line 63   Delete "M-methyl-pyrrollidone" and substitute --N-methyl-pyrrolidone--

Col. 17, line 50   After "example," add --crushed and fractionated natural rocks such as calcite,--

Col. 37, line 59   Add page - 46-

Table 4 - Continuation

| Example No. | 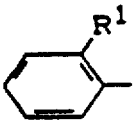 R¹ | R² | Physical constants |
|---|---|---|---|
| II-59 |  Cl | 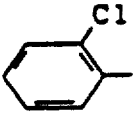 t.-H₉C₄ | Wax |
| II-60 | 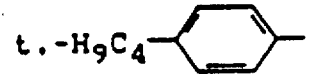 CH₃ | 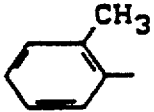 O₂N | |
| II-61 |  F |  | |

UNITED STATES PATENT AND TRADEMARK OFFICE
CERTIFICATE OF CORRECTION

PATENT NO. : 4,846,879

DATED : July 11, 1989

INVENTOR(S) : Fest et al.

It is certified that error appears in the above-identified patent and that said Letters Patent is hereby corrected as shown below:

Table 4-continued

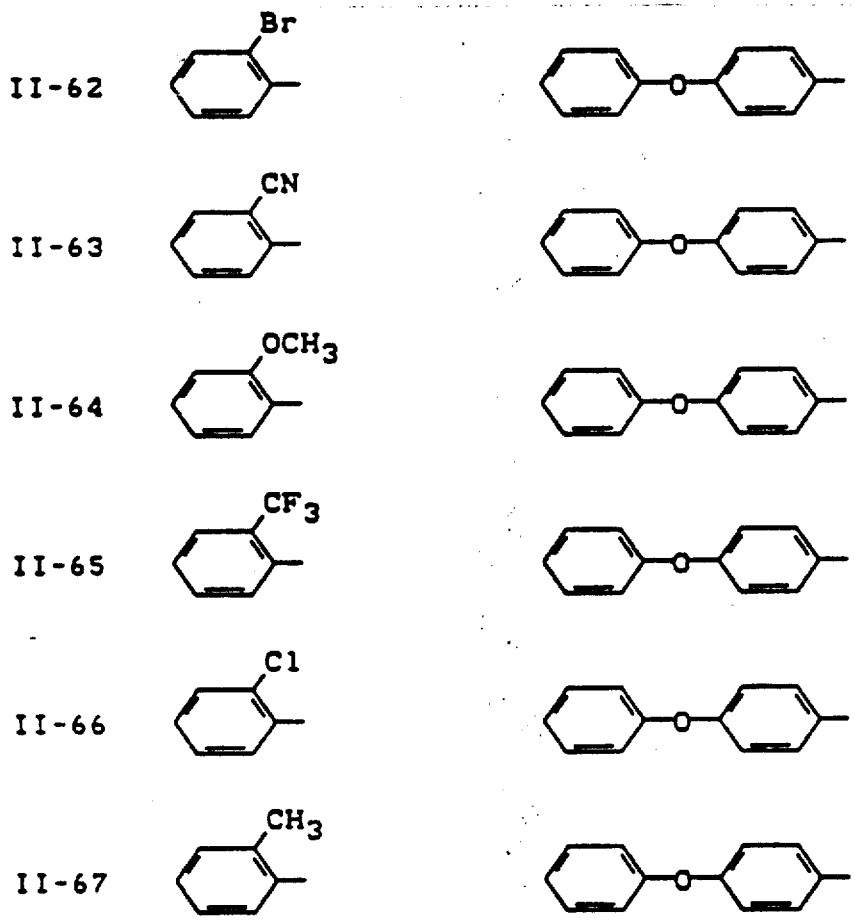

UNITED STATES PATENT AND TRADEMARK OFFICE
CERTIFICATE OF CORRECTION

PATENT NO. : 4,846,879

DATED : July 11, 1989

INVENTOR(S) : Fest et al.

It is certified that error appears in the above-identified patent and that said Letters Patent is hereby corrected as shown below:

Col. 40, line 35  Under physical constants add--Melting point
Ex No. II-101                 120°C--

Col. 42, line 13  Under Physical constants add--Melting point
Ex No. II-122                 171°C--

Col. 45, line 38  Delete "ditotyledon" and substitute --dicotyledon--

Col. 47, lines 9-18  Delete "of the formula" and substitute --according to claim 1-- and delete "formula

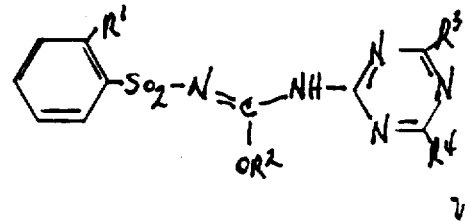

Signed and Sealed this

Twenty-ninth Day of January, 1991

*Attest:*

HARRY F. MANBECK, JR.

*Attesting Officer*    *Commissioner of Patents and Trademarks*